United States Patent [19]

Scholl

[11] Patent Number: 5,354,888

[45] Date of Patent: Oct. 11, 1994

[54] PROCESS FOR THE PRODUCTION OF ORGANIC CARBODIIMIDES AND THEIR USE AS STABILIZERS FOR PLASTICS

[75] Inventor: Hans-Joachim Scholl, Cologne, Fed. Rep. of Germany

[73] Assignee: Bayer Aktiengesellschaft, Leverkusen, Fed. Rep. of Germany

[21] Appl. No.: 186,188

[22] Filed: Jan. 24, 1994

[30] Foreign Application Priority Data

Feb. 1, 1993 [DE] Fed. Rep. of Germany ....... 4302697

[51] Int. Cl.$^5$ ............................................. C07C 267/00
[52] U.S. Cl. .................................................. 564/252
[58] Field of Search ......................................... 564/252

[56] References Cited

U.S. PATENT DOCUMENTS 2,853,473  9/1958  Campbell et al. .................. 260/77.5
4,014,935  3/1977  Ibbotson ............................. 564/252

FOREIGN PATENT DOCUMENTS 1157401  10/1963  Fed. Rep. of Germany .

Primary Examiner—Peter O'Sullivan
Attorney, Agent, or Firm—Joseph C. Gil; Lyndanne M. Whalen

[57] ABSTRACT

Organic carbodiimides are produced by carbodiimidization of isocyanate groups with catalysts of the phospholine type. At the end of the carbodiimidization reaction, the catalyst system is removed by introducing carbon dioxide in vacuo at temperatures of from about 100° to about 250° C. The carbodiimides produced by this process are particularly useful as stabilizers for plastics.

1 Claim, No Drawings

PROCESS FOR THE PRODUCTION OF ORGANIC CARBODIIMIDES AND THEIR USE AS STABILIZERS FOR PLASTICS

BACKGROUND OF THE INVENTION

The present invention relates to a new process for the production of organic carbodiimides and to the use of these carbodiimides for stabilizing plastics against hydrolysis.

Carbodiimides can be readily produced with catalysts from the phospholine oxide series by the basic process disclosed in U.S. Pat. No. 2,853,473.

This ability to catalyze easily is very desirable because it makes it possible to carry out the carbodiimidization reaction under moderate conditions. No process which ensures effective and perfect separation of the phospholine oxide catalyst from the end products of the carbodiimidization process is disclosed in the prior art.

There is a commercial need for storable carbodiimides which serve as hydrolysis stabilizers and do not cause troublesome secondary reactions, even at relatively high temperatures caused by rest activity of the catalytic material. This catalytic material cannot be removed simply by distillation. For example, in the production of distillable carbodiimides such as 2,6,2'-,6'-tetraisopropyl diphenyl carbodiimide from 2,6-diisopropylphenyl isocyanate with a technical mixture of 1-methyl-1-phospha-2-cyclopentene-1-oxide and 1-methyl-1-phospha-3-cyclopentene-1-oxide as catalyst, the catalyst cannot be removed completely by simple distillation. The product therefore remains "residually active", even when a relatively large head fraction is removed and even where carrier gases, such as nitrogen or argon, are present.

German Auslegeschrift 1 156 401 (U.S. Pat. No. 3,502,722) is directed to the production of storage stable carbodiimides using KOH, for example, as the catalyst to prevent troublesome residual activities. By comparison with phospholine oxides as catalysts, however, this process has serious disadvantages. Large quantities of catalyst and rigorous reaction conditions are required and technically inferior colored end products are obtained. This process cannot be adopted for non-distillable (poly)carbodiimides.

SUMMARY OF THE INVENTION

It is an object of the present invention to provide a process for the production of storage stable carbodiimides without any rest activity, caused by the used catalytic material.

It is also an object of the present invention to provide a process in which carbodiimides are produced with a catalyst which is readily separated from the product carbodiimide.

It is a further object of the present invention to provide a process for the production of carbodiimides which are useful as stabilizers for plastics.

It is another object of the present invention to provide a process for removing a phospholine type catalyst from a carbodiimide reaction mixture.

These and other objects which will be apparent to those skilled in the art are accomplished by subjecting an isocyanate to carbodiimidization conditions in the presence of a phospholine oxide catalyst. Carbon dioxide is introduced in vacuo into the reaction vessel at a temperature of from about 100° to about 250° C. to remove the catalyst system when the desired degree of carbodiimidization has been achieved.

DETAILED DESCRIPTION OF THE INVENTION

The present invention relates to a process for the production of organic carbodiimides by carbodiimidization of isocyanate groups with catalysts of the phospholine oxide type. When the desired degree of carbodiimidization has been achieved, the catalyst system is separated off by introduction of carbon dioxide in vacuo at temperatures of from about 100° to about 250° C. The present invention also relates to the organic carbodiimides obtained by this process and to the use of these organic carbodiimides for stabilizing plastics against hydrolysis.

Any of the known organic isocyanates, particularly those mentioned in the disclosures described above, may be used as starting materials for the process of the present invention.

Preferred organic isocyanates include the aromatic monoisocyanates and diisocyanates which are substituted in each of the positions which are ortho to the isocyanate group (described in German Auslegeschrift 1 156 401 (U.S. Pat. No. 3,502,722)). 2,6-diisopropylphenyl isocyanate and 2,4,6-triisopropylphenyl-1,3-diisocyanate are particularly preferred.

The carbodiimidization process of the present invention is carried out in the presence of the above-mentioned highly effective catalysts from the phospholine series. An example of such catalysts is the commercially available mixture of phospholine oxides corresponding to the formulae:

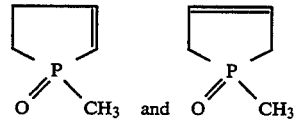

The quantity of catalyst used depends upon the quality of the starting isocyanates. The quantity of catalyst required to carbodiimidize a particular isocyanate may readily be determined in a preliminary test.

In the process of the present invention, the carbodiimidization reaction is carried out at a temperature of from about 50° to about 250° C., preferably at a temperature of from about 80° to about 200° C. The optimum reaction temperature is dependent upon the type of starting isocyanates used and may be determined in a simple preliminary test.

The carbodiimidization reaction is generally terminated on reaching a degree of carbodiimidization (degree of carbodiimidization = percentage of carbodiimidized isocyanate groups, based on the total quantity of isocyanate groups present in the starting isocyanate) of from about 20 to about 100%, preferably from about 30 to about 99%. The degree of carbodiimidization may be determined during the process of the present invention by measurement of the decreasing NCO content. An NCO content of 0 (i.e., the end of the carbodiimidization reaction) signifies a degree of carbodiimidization of 100. On reaching the required degree of carbodiimidization, carbon dioxide is introduced into the reaction mixture in vacuo at a temperature of from about 100° to about 250° C., preferably from about 150 to about 230° C. The introduction of carbon dioxide is continued until the organic carbodiimide shows no more residual activity. The absence of residual activity may be determined analytically, for example, by failure to detect traces of phosphorus. The absence of activity may also be determined by an "accelerated chemical test" in which 20% by weight (for example) of carbodiimide prepared in accordance with the present invention is stirred in 2,4-diisocyanatotoluene for 30 minutes at 140° C. In the absence of $CO_2$ or in the absence of a significant increase in the refractive index, the carbodiimide has no residual activity so that the introduction of $CO_2$ can be terminated. Reaction conditions and the introduction time for carbon dioxide are, of course, best determined in a preliminary test.

For non-distillable (poly)carbodiimides, the carbodiimide of the present invention may be directly used after introduction of the carbon dioxide and, optionally, after subsequent degassing in vacuo.

For distillable carbodiimides, the introduction of carbon dioxide is preferably continued until the removal of a first fraction is complete. The "sump product" thus freed from residual activity is then conventionally distilled.

The organic carbodiimides prepared in accordance with the present invention are valuable hydrolysis stabilizers for plastics.

Having thus described my invention, the following Examples are given as being illustrative thereof. All parts and percentages given in these Examples are parts by weight or percentages by weight, unless otherwise indicated.

EXAMPLES

The following materials were used to produce the carbodiimides of Examples 1 through 3:

CATALYST: Technical mixture of 1-methyl-1-phospha-2-cyclopentene-1-oxide and 1-methyl-1-phospha-3-cyclopentene-1-oxide which are represented by the formulae

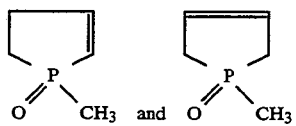

ISOCYANATE 1: 2,6-diisopropylphenyl isocyanate
ISOCYANATE 2: 2,4,6-triisopropylphenyl-1,3-diisocyanate.

Example 1

Processing According to the Invention 0.1 g of CATALYST were added to 812 g (4 mol) of ISOCYANATE 1, followed by stirring for 27 hours at 170° C. The NCO content fell from 20.7% to 0.5%. A head fraction was then removed in vacuo (0.4 mbar) with introduction of $CO_2$ until the internal temperature had risen to 170° C. The introduction of $CO_2$ was terminated and the carbodiimide according to the invention was subsequently distilled over.

(Bp. 172°–182° C./0.3 mbar):
Head Fraction: 108 g (15%)
Main fraction: 598 g (83%), carbodiimide according to the invention.

Example 2

Comparison Example

Example 1 was repeated in exactly the same way with the exception that distillation was carried out conventionally with no introduction of $CO_2$.
Head fraction: 110 g (15.3%)
Main fraction: 595 g (82.6%), carbodiimide with prohibitive residual activity

Example 3

"Accelerated Test" for Residual Activity

Carbodiimides of the 2,6,2',6'-tetraisopropyl diphenyl carbodiimide (I) type which were produced by processes different from that used in Example 1 (which processes are described below) were tested as follows for residual activity:

36 g of carbodiimide (I) (0.1 mol) were stirred for 30 minutes at 140° C. into 174 g (1 mol) of 2,4-diisocyanatotoluene. Where residual activity was present, $CO_2$ was eliminated and the refractive index $n_D$ underwent a distinct increase. The data are set out in Table 1:

TABLE 1

| Example | $CO_2$ | Increase in refractive index [$n_D^{23°C.}$, 0-value, 30 mins.] | $\Delta n_D^{23°C.} \cdot 10^4$ |
|---|---|---|---|
| 3 a | − | 1.5662→1.5672 | 10 |
| 3 b | + | 1.5662→1.5712 | 50 |
| 3 c | − | 1.5662→1.5672 | 10 |
| 3 d | + | 1.5662→1.5720 | 58 |

+ indicates $CO_2$ present
− indicates no $CO_2$ present

Example 3 a

The carbodiimide used in this Example 3a (I) was prepared in accordance with the procedure disclosed in German Auslegeschrift 1 156 401 (U.S. Pat No. 3,502,722) and which is commercially available under the trade name of Strabaxol ®1 (a product of Rhein-Chemie Rheingau GmbH). The carbodiimide was produced without using phospholine oxide as the catalyst (KOH-catalyst). Example 3a is the comparison standard.

Example 3 b

Carbodiimide (I) was prepared by the same procedure as was used in Example 3a with the exception that 0.46 ppm CATALYST were added. This small amount of CATALYST was sufficient to provoke distinct residual reactivity.

Example 3 c

The carbodiimide from Example 1, according to the invention, had no residual activity compared with Example 3 a.

Example 3 d

The carbodiimide from Example 2, a comparison product, showed distinct residual activity. This example demonstrates the advantage critical to the invention of introducing $CO_2$.

The following Examples 4–6 demonstrate the excellent stabilizing effect of the carbodiimides produced in accordance with the invention in elastomers.

Example 4

Comparison Example, No Addition of Carbodiimide 1000 g (0.5 mol) of a dehydrated polyester based on adipic acid ethylene glycol/butane-1,4-diol (ratio by weight 1:1), number average molecular weight 2000 g/mol (OH value 56), were heated to 125° C. and intensively stirred with 180 g (0.86 mol) of 1,5-naphthylene diisocyanate (NDI). After stirring for 2 minutes, the mixture was degassed in vacuo and, after 15 minutes, the NCO prepolymer formed was stirred with 20 g (0.22 mol) of butane-1,4-diol. The reaction mixture which remained liquid for about 3.5 minutes was poured into a mold preheated to 110° C. in which it solidified after about 30 minutes.

Example 5

Application Example with Addition of the Carbodiimide of Example 1 According to the Invention Example 4 was repeated with the exception that 20 g of the carbodiimide of Example 1 were added to the polyester.

Example 6

Comparison Example with Addition of the Carbodiimide from Example 3a

Example 4 was repeated with the exception that 20 g of the carbodiimide from Example 3a were added to the polyester.

The formulations and processing parameters used in each of Examples 4–6 are set out in Table 2.

The physical properties of the products obtained in each of Examples 4–6 are set out in Table 3.

TABLE 2

|  | Example 4 | Example 5 | Example 6 |
|---|---|---|---|
| Polyester (g) | 1000 | 1000 | 1000 |
| NDI (g) | 180 | 180 | 180 |
| Carbodiimide of Example 1 (g) | — | 20 | — |
| Carbodiimide of Example 3 a | — | — | 20 |
| Butane-1,4-diol (g) | 20 | 20 | 20 |
| Mold temperature (°C.) | 110 | 110 | 110 |
| Caasting time (min.) | 3.5 | 1.8 | 1.8 |

TABLE 3

| Property | Test standard | Ex. 4 | Ex. 5 | Ex. 6 |
|---|---|---|---|---|
| Shore hardness A/D | DIN 53 505 | 82 | 82 | 82 |
| Resilience (%) | DIN 53 512 | 60 | 60 | 60 |
| Abrasion loss (mm$^3$) | DIN 53 516 | 40 | 40 | 40 |
| Compression set (%) | DIN 53 517 | 20 | 23 | 23 |
| Shore A/D after hydrolysis test (80° C./14 days) | | Test specimen destroyed by hydrolysis | 75 | 74 |

Example 7

Process According to the Invention for the Production of a Non-Distillable polycarbodiimide 0.14 g of CATALYST were added to 1000 g (3.5 mol) of ISOCYANATE 2 and stirred for 4 hours at 160° C. $CO_2$ was then introduced in vacuo for 60 minutes (2 mbar, 175° C.).

The residue thus treated was a polycarbodiimide according to the present invention (NCO content: 11.9%) which did not show any residual activity in the "accelerated test". Accelerated test conditions 12 g of the polycarbodiimide obtained in accordance with Example 7 were stirred into 58 g of 2,4-diisocyanatotoluene at 140° C. Even after 3 hours, the initial NCO value of 41% was unchanged.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of organic carbodiimides comprising
   a) carbodiimidizing an isocyanate with a phospholine oxide catalyst and
   b) upon completion of a), removing the catalyst system by introducing carbon dioxide in vacuo at a temperature of from about 100° to about 250° C.

* * * * *